United States Patent [19]

Ohtsuki et al.

[11] Patent Number: 5,266,306
[45] Date of Patent: Nov. 30, 1993

[54] ORAL COMPOSITION

[75] Inventors: Hidehiko Ohtsuki, Takatsuki; Tomomi Fujita, Suita, both of Japan

[73] Assignee: Sunstar Kabushiki Kaisha, Osaka, Japan

[21] Appl. No.: 828,793

[22] PCT Filed: May 23, 1991

[86] PCT No.: PCT/JP91/00691

§ 371 Date: Jan. 28, 1992

§ 102(e) Date: Jan. 28, 1992

[87] PCT Pub. No.: WO91/18585

PCT Pub. Date: Dec. 12, 1991

[30] Foreign Application Priority Data

May 29, 1990 [JP] Japan .................. 2-139125

[51] Int. Cl.$^5$ .......................... A61K 7/16; A61K 7/22
[52] U.S. Cl. .......................................... 424/54; 424/49
[58] Field of Search ........................ 424/49–58

[56] References Cited

U.S. PATENT DOCUMENTS

| | | | |
|---|---|---|---|
| 2,689,170 | 9/1954 | King | 424/54 |
| 2,757,125 | 7/1956 | Mudrak | 424/54 |
| 2,772,203 | 11/1956 | Salzmann | 424/54 |
| 2,772,204 | 11/1956 | King | 424/54 |
| 2,842,479 | 7/1958 | Jungermann | 424/54 |
| 2,909,535 | 10/1959 | Jungermann | 424/54 |
| 4,618,488 | 10/1986 | Maeyama et al. | 424/49 |
| 4,661,342 | 4/1987 | Yamazaki et al. | 424/54 |
| 4,828,824 | 5/1989 | Grollier | 424/52 |
| 4,865,839 | 9/1989 | Saso | 424/54 |
| 5,017,364 | 5/1991 | Mitsutake et al. | 424/54 |
| 5,035,881 | 7/1991 | Mori et al. | 424/54 |

FOREIGN PATENT DOCUMENTS

| | | |
|---|---|---|
| 0422803 | 4/1991 | European Pat. Off. |
| 3705434 | 8/1987 | Fed. Rep. of Germany |
| 48-1140 | 1/1973 | Japan |
| 53-86047 | 7/1978 | Japan |
| 1352420 | 5/1974 | United Kingdom |
| 9116033 | 10/1991 | World Int. Prop. O. |

Primary Examiner—Shep K. Rose
Attorney, Agent, or Firm—Wegner, Cantor, Mueller & Player

[57] ABSTRACT

An oral composition comprising cetylpyridinium chloride and a $N^\alpha$-longer acyl basic amino acid lower alkyl ester or a salt thereof. The oral composition of the present invention promotes adsorption of cetylpyridinium chloride as a bactericide to the surfaces of teeth and shows excellent prevention of formation of dental plaque and dental caries.

3 Claims, No Drawings

ORAL COMPOSITION

FIELD OF THE INVENTION

The present invention relates to a composition for the oral cavity. More particularly, it relates to an oral composition wherein adsorption of cetylpyridinium chloride as a bactericide to the surfaces of teeth is promoted.

BACKGROUND OF THE INVENTION

Dental plaque is formed by adsorption and propagation of intraoral bacteria such as *Streptococcus mutans* and the like on the surfaces of teeth. It is well known that dental plaque is the cause of dental caries and is also the cause of gingivitis or alveolar pyorrhea. Therefore, it is important to remove dental plaque and to prevent adhesion of it (plaque control) for oral sanitation.

Among the plaque control methods, the method which is performed most commonly is that for removing dental plaque mechanically by brushing, that is, by using a toothbrush. However, in order to remove dental plaque completely by brushing, high-level brushing technique is needed. In practice, almost all people are conducting insufficient brushing and, therefore, the rate of diseases such as dental caries, gingivitis and alveolar pyorrhea is not reduced despite brushing.

Accordingly, in order to compensate brushing, or to substitute for brushing, a chemical plaque control method has been studied. The pyridinium compounds having $C_{8-18}$ straight or blanched chain alkyl group are known. Among them, the compound of which efficacy and safety are clinically acknowledged is cetylpyridinium chloride.

It is known that cetylpyridinium chloride is a compound represented by the formula:

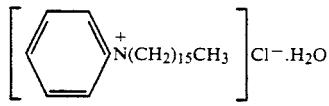

and it has a bactericidal action and is easily to adsorbed to oral mucosa or the surfaces of teeth. Thereby, it is considered that adsorption of intraoral bacteria to the surfaces of teeth is prevented and, further, formation of dental plaque is prevented. However, a study on promoting adsorption of such cetylpyridinium chloride to the surfaces of teeth or on improving it's effect has not been performed yet.

The present inventors have intensively studied to promote retention of cetylpyridinium chloride in the oral cavity, particularly adsorption of it to the surfaces of teeth and to enhance the effect of preventing formation of bacterial plaque. As a result, it has been found that, when cetylpyridinium chloride is used in combination with an $N^\alpha$-longer acyl basic amino acid lower alkyl ester or a salt thereof, adsorption of cetylpyridinium chloride to the surfaces of teeth is greatly enhanced. Thus, the present invention has been completed.

DISCLOSURE OF THE INVENTION

According to the present invention, there is provided an oral composition comprising cetylpyridinium chloride and an $N^\alpha$-longer acyl basic amino acid lower alkyl ester or a salt thereof. According to the present invention, an oral composition which promotes adsorption of cetylpyridinium chloride to the surfaces of teeth and has excellent effect for preventing formation of dental plaque and dental caries can be obtained.

Cetylpyridinium chloride is normally formulated into the composition in an amount of more than 0.002 % by weight, preferably more than 0.01 % by weight. In view of bactericidal effect, the upper limit of the amount of cetylpyridinium chloride is not specifically limited. Considering the fact that cetylpyridinium chloride has a bitter taste and is likely to color teeth when the amount is too large, or influence on oral mucosa and the like, it is normally preferred that the amount is less than 1 % by weight.

As the basic amino acid part of the $N^\alpha$-longer acyl basic amino acid lower alkyl ester to be used, ornithine, lysine and arginine are particularly preferred and it may be either an optical isomer or racemate thereof. The acyl group thereof is a saturated or unsaturated natural or synthetic fatty acid residue having 8 to 22 carbon atoms, for example, it may be a natural system mixed fatty acid residue such as coconut oil fatty acid, tallow fatty acid residue and the like, in addition to a mono-fatty acid residue such as lauroyl, myristyl, stearoyl group and the like. Further, it may also be a lower alkyl ester, such as methyl ester, ethyl ester and propyl ester are.

Examples of the salt of the $N^\alpha$-longer basic amino acid lower alkyl ester include an inorganic acid salt such as hydrochloride, sulfate, etc. or an organic acid salt such as acetate, tartrate, citrate, p-toluenesulfonate, fatty acid salt, acidic amino acid salt, etc. Among them, glutamate, pyroglutamate, acetate and citrate are preferred.

In the present invention, the $N^\alpha$-longer basic amino acid lower alkyl ester or a salt thereof is that which promotes adsorption of cetylpyridinium chloride to the surfaces of teeth. The weight ratio thereof is at least 1/5, normally 1/5 to 10 based on the weight of cetylpyridinium chloride. When the ratio is too small, the effect of promoting adsorption of cetylpyridinium chloride to teeth becomes insufficient.

The oral composition of the present invention can be prepared in the form of tooth powder, dentifrice, mouthwash, troches and the like by formulating desired ingredients according to a conventional method and, further, it can be sprayed in the oral cavity as an aerosol. Further, it can be used for a liniment and also used after being impregnated in a dental floss or toothpick.

The other ingredients formulated may be any ingredients which can be used in this kind of compositions in so far as they do not inhibit adsorption of cetylpyridinium chloride to the surfaces of teeth and its bactericidal action. In the case of using vesicants or solubilizers, anionic ingredients are not preferred. It has been found that, when using nonionic or cationic ingredients, particularly, polyoxyethylene polyoxypropylene glycol, ethylenediaminetetrapolyoxyethylene polyoxypropylene glycol and the like, the effect of cetylpyridinium chloride is further improved.

EXAMPLES

The following Experiments and Examples further illustrate the present invention in detail but are not to be construed to limit the scope thereof. In Experiments and Examples, all percentages are by weight unless otherwise stated.

Experiment 1

Adsorption test of cetylpyridinium chloride to the surfaces of teeth

The composition of enamel of the surfaces of teeth consists of inorganic mineral (97 %), organic material (1%) and water content (2 %), and a main ingredient of the mineral is calcium phosphate which is referred to as hydroxyapatite $[Ca_{10}(PO_4)_6(OH)_2]$.

As a model of enamel of teeth, that obtained by dipping a hydroxyapatite disc [Bio-Gel HTP manufactured by Bio. Rad. Laboratories Co., U.S.A., 13 mm$\phi$ ×250 mg; prepared by making tablets at 150 kg/cm$^2$ and sintering at 600° C. for 6 hours] in human saliva at 37° C. for 18 hours was used. By dipping in saliva, saliva mucoprotein, etc. was adsorbed to the surface of hydroxyapatite to be allowed to simulate an actual state of tooth enamel wetted with saliva. This hydroxyapatite disc treated with saliva was placed in a test tube, followed by the addition of an aqueous 0.05 % cetylpyridinium chloride (manufactured by Merck Co.) solution (1 ml) and shaking at 37° C. for 30 minutes. Thereafter, it was washed with water (6 ml) and extracted with an extraction solvent [50 mM sodium lauryl sulfate, 40 mM citrate buffer (pH 3.0)/acetonitrile =30/70] to form a sample for high speed liquid chromatography. In the case of high speed liquid chromatography, Lichrosorb RP select B (4.0 mm$\phi$ ×250 mm) was used as a separation column and a extraction solvent was used as an eluent. The flow rate was 1 ml/minutes and detection of cetylpyridinium was conducted by measuring absorbance with 258 nm. Further, by using a calibration curve made by a standard solution of cetylpyridinium chloride, the amount of cetylpyridinium chloride was determined.

Likewise, after an apatite disc treated with saliva was dipped in a mixed solution in which various additives as shown in Table 1 were added to 0.05 % cetylpyridinium chloride in an amount of 0.1 %, respectively, the amount of cetylpyridinium chloride was determined. Further, regarding N$^\alpha$-cocoyl-L-arginine ethyl ester pyrrolidone carboxylate among the additives which showed the effect for enhancing the amount of cetylpyridinium chloride adsorbed on the apatite disc, by varying in amount between 0.005, 0.01 and 0.05 %, respectively, the influence of the concentration on the amount of cetylpyridinium chloride adsorbed was confirmed. The results are also shown in Table 1.

TABLE 1

| Compound | Amount of cetylpyridinium chloride ($\mu$g/disc) | |
|---|---|---|
| | Initial | After 3 hours |
| 0.05% Cetylpyridinium chloride | 170 | 63 |
| 0.05% Cetylpyridinium chloride + 0.01% N$^\alpha$-cocoyl-L-arginine methyl ester hydrochloride | 411 | 321 |
| 0.05% Cetylpyridinium chloride + 0.1% N$^\alpha$-lauroyl-L-arginine methyl ester pyrrolidone carboxylate | 436 | 336 |
| 0.05% Cetylpyridinium chloride + 0.1% N$^\alpha$-cocoyl-L-arginine ethyl ester pyrrolidone carboxylate | 438 | 346 |
| 0.05% Cetylpyridinium chloride + 0.1% N$^\alpha$-palmitol-L-lysine methyl ester acetate | 424 | 330 |
| 0.05% Cetylpyridinium chloride + 0.1% sodium N$^\alpha$-lauroyl methyl taurine | 59 | 18 |
| 0.05% Cetylpyridinium chloride + 0.1% sodium N$^\alpha$-lauroyl-methyl-b-alanine | 173 | 60 |
| 0.05% Cetylpyridinium chloride + 0.005% N$^\alpha$-cocoyl-L-arginine ester pyrrolidone carboxylate | 175 | 119 |
| 0.05% Cetylpyridinium chloride + 0.01% N$^\alpha$-cocoyl-L-arginine ethyl ester pyrrolidone carboxylate | 331 | 242 |
| 0.05% Cetylpyridinium chloride + 0.05% N$^\alpha$-cocoyl-L-arginine ethyl ester pyrrolidone carboxylate | 392 | 294 |

As is shown in Table 1, when a N$^\alpha$-longer acyl basic amino acid lower alkyl ester is formulated, cetylpyridinium chloride is specifically adsorbed to the hydroxyapatite disc and it is necessary that the weight ratio is more than 1/5 based on the weight of cetylpyridinium chloride.

EXPERIMENT 2

Since cetylpyridinium chloride is sometimes inactivated in the case of forming a salt with an acidic substance, retention of bactericidal activity was also tested as follows.

Regarding a sample wherein adsorption of cetylpyridinium chloride to the hydroxyapatite disc was enhanced by adding the N$^\alpha$-longer acyl basic amino acid lower alkyl ester, a disc was suspended to a 5 % sucrose BHI medium. Then, one loopful of the *Streptococcus mutans* ATCC 25175 strain was inoculated and cultivated at 37° C. for 18 hours. As a result, adhesion of plaque to the hydroxyapatite disc was not observed and it was confirmed that cetylpyridinium chloride adsorbed on the hydroxyapatite disc retains bactericidal activity.

EXAMPLE 1

According to the following formulation, a toothpaste was prepared by degassing, kneading and stirring according to a conventional method.

| Ingredients | % by weight |
|---|---|
| Calcium hydrogenphosphate | 20.0 |
| Polyoxyethylene polyoxypropylene glycol | 30.0 |
| Glycerin | 10.0 |
| Cetylpyridinium chloride | 0.1 |
| N$^\alpha$-lauroyl-L-arginine methyl ester pyrrolidone carboxylate | 0.05 |
| Saccharin sodium | 0.2 |
| Flavor | 1.0 |
| Distilled water | up to 100% |

EXAMPLE 2

According to the following formulation, a toothpaste was prepared by degassing, kneading and stirring according to a conventional method.

| Ingredients | % by weight |
|---|---|
| Calcium carbonate | 35.0 |
| Hydroxyethylcellulose | 1.5 |
| Ethylenediamine tetrapolyoxy- | 5.0 |

-continued

| Ingredients | % by weight |
| --- | --- |
| ethylene polyoxypropylene glycol | |
| Sorbitol | 30.0 |
| Cetylpyridinium chloride | 0.01 |
| $N^\alpha$-cocoyl-L-arginine methyl ester hydrochloride | 0.01 |
| Saccharin sodium | 0.1 |
| Flavor | 1.0 |
| Distilled water | up to 100% |

EXAMPLE 3

According to the following formulation, a liquid mouthwash was prepared by mixing with stirring according to a conventional method.

| Ingredients | % by weight |
| --- | --- |
| Ethanol | 10.0 |
| Glycerin | 10.0 |
| Polyoxyethylene polyoxypropylene glycol | 1.5 |
| Saccharin sodium | 0.02 |
| Cetylpyridinium chloride | 0.05 |
| $N^\alpha$-cocoyl-L-arginine ethyl ester pyrrolidone carboxylate | 0.1 |
| Flavor | 0.3 |
| Distilled water | up to 100% |

EXAMPLE 4

A yarn of 630 deniers comprising a plurality of fine denier filaments of 6,6-nylon being twisted was dipped in the mixed solution of the following formulation, passed through a drying tube at 50° C. and spooled with vaporizing ethanol to produce a dental floss.

| Ingredients | % by weight |
| --- | --- |
| Cetylpyridinium chloride | 5.0 |
| $N^\alpha$cocoyl-L-arginine ethyl ester pyrrolidone carboxylate | 10.0 |
| Ethanol | 85.0 |

What is claimed is:

1. An oral composition consisting essentially of a bactericidal effective amount of cetylpyridinium chloride and a $N^\alpha$-longer acyl basic amino acid lower alkyl ester or a salt thereof in an amount effective to promote the adsorption of cetylpyridinium chloride to the surfaces of teeth, wherein the amount of cetylpyridinium chloride is from 0.002% to 1% by weight of the composition.

2. An oral composition according to claim 1, wherein the weight ratio of the $N^\alpha$-longer acyl basic amino acid lower alkyl ester to cetylpyridinium chloride is from 1/5 to 10.

3. An oral composition according to claim 2, wherein the $N^\alpha$-longer acyl basic amino acid lower alkyl ester is selected from the group consisting of $N^\alpha$-cocoyl-L-arginine methyl ester hydrochloride, $N^\alpha$-lauroyl-L-arginine methyl ester pyrrolidone carboxylate, $N^\alpha$-cocoyl-L-arginine ethyl ester pyrrolidone carboxylate, and $N^\alpha$-palmitoyl-L-lysine-methyl ester acetate.

* * * * *